US009534991B2

(12) United States Patent
Kaufmann et al.

(10) Patent No.: US 9,534,991 B2
(45) Date of Patent: Jan. 3, 2017

(54) HANDHELD SAMPLING-REMOVAL HEAD, ANALYSIS ARRANGEMENT AND METHOD FOR CHARACTERIZING AN AEROSOL

(75) Inventors: Andreas Kaufmann, Kirchzarten (DE); Florian Beck, Stuhlingen (DE)

(73) Assignee: TESTO AG, Lenzkirch (DE)

( * ) Notice: Subject to any disclaimer, the term of this patent is extended or adjusted under 35 U.S.C. 154(b) by 326 days.

(21) Appl. No.: 14/004,564

(22) PCT Filed: Mar. 6, 2012

(86) PCT No.: PCT/EP2012/000996

§ 371 (c)(1),
(2), (4) Date: Sep. 11, 2013

(87) PCT Pub. No.: WO2012/123077

PCT Pub. Date: Sep. 20, 2012

(65) Prior Publication Data

US 2014/0000343 A1 Jan. 2, 2014

(30) Foreign Application Priority Data

Mar. 11, 2011 (DE) ........................ 10 2011 013 698

(51) Int. Cl.

| | |
|---|---|
| ***G01N 30/20*** | (2006.01) |
| ***G01N 1/38*** | (2006.01) |
| ***G01N 1/22*** | (2006.01) |
| *G01N 15/06* | (2006.01) |

(52) U.S. Cl.

CPC .............. *G01N 1/38* (2013.01); *G01N 1/2247* (2013.01); *G01N 1/2273* (2013.01); *G01N 15/06* (2013.01); *G01N 2001/2264* (2013.01)

(58) Field of Classification Search

None

See application file for complete search history.

(56) References Cited

U.S. PATENT DOCUMENTS

| | | | | |
|---|---|---|---|---|
| 3,223,123 | A * | 12/1965 | Young | 137/625.46 |
| 4,333,500 | A * | 6/1982 | Broerman | 137/863 |
| 4,726,237 | A * | 2/1988 | Yung | 73/864.83 |
| 5,270,212 | A * | 12/1993 | Horiuchi et al. | 436/45 |
| 6,976,383 | B2 * | 12/2005 | Petro | B01D 15/08 422/504 |
| 8,474,304 | B2 | 7/2013 | Knopf et al. | |

(Continued)

FOREIGN PATENT DOCUMENTS

| | | |
|---|---|---|
| AT | 009603 | 12/2007 |
| DE | 10140013 | 3/2003 |

(Continued)

*Primary Examiner* — Robert R Raevis

(74) *Attorney, Agent, or Firm* — Volpe and Koenig, P.C.

(57) ABSTRACT

In a sampling head (1) of an analysis arrangement (31), provision is made that a sample stream delivered via a sampling line (2) and a dilution air stream delivered through a dilution air inlet (4) are mixed together in a dilution unit (3) in such a way that a volumetric quantity entrained in at least one receiving space moved along by a movable element (8) between the sampling stream and the dilution air stream are exchanged with each other, wherein the analysis arrangement (31) has a gas analyzer (35) for the analysis of the slightly diluted sample stream and a particle determination unit (32) for the analysis of the enriched dilution air stream.

20 Claims, 6 Drawing Sheets

(56) References Cited

U.S. PATENT DOCUMENTS

| | | | |
|---|---|---|---|
| 2004/0202578 A1 | 10/2004 | Burtscher et al. | |
| 2007/0092976 A1* | 4/2007 | Watson et al. | 436/181 |
| 2009/0049934 A1 | 2/2009 | Bergmann et al. | |
| 2010/0284006 A1 | 11/2010 | Socha et al. | |

FOREIGN PATENT DOCUMENTS

| | | |
|---|---|---|
| DE | 10236160 | 3/2004 |
| DE | 102009032752 | 1/2011 |
| EP | 1467194 | 10/2004 |
| EP | 1600772 | 11/2005 |
| EP | 2264423 | 12/2010 |
| JP | 6076641 | 5/1985 |

* cited by examiner

HANDHELD SAMPLING-REMOVAL HEAD, ANALYSIS ARRANGEMENT AND METHOD FOR CHARACTERIZING AN AEROSOL

BACKGROUND

The invention relates to a hand-held sampling head for collecting a sample of an aerosol containing suspended particles, with a sampling line and with an integrated dilution unit which is connected to the sampling line and which has a dilution air inlet.

Sampling heads of this kind are known in analysis arrangements for analyzing or characterizing aerosols, wherein the sampling head is used to collect a sample volume from a larger sample reservoir or from an aerosol flow. Dilution air or a dilution gas is often sprayed into the collected sample volume in the dilution unit in order to permit or facilitate a subsequent analysis.

Accordingly, the invention further relates to an analysis arrangement for characterizing an aerosol.

The invention relates finally to a method for characterizing an aerosol, wherein the aerosol has a carrier gas and suspended particles received therein.

The revised version of the 1st German Federal Emmissions Control Act stipulates a reduction of the limit value of the dust and particle emissions in small and medium-sized solid-fuel plants.

SUMMARY

The object of the invention is to make available a measurement appliance that is easy to handle and that is suitable for a wide range of uses.

In a hand-held sampling head of the type mentioned at the outset, this object is achieved, according to the invention, in that the dilution unit has a first element with a first contact face and a second element with a second contact face, which are arranged to be movable relative to each other and which are in flat contact with each other via their respective contact faces, in that a sample channel open toward the second element is formed in the first element in the first contact face and is connected to the sampling line, in that a dilution air channel open toward the second element is formed in the first element in the first contact face and is connected to the dilution air inlet, and in that at least one receiving space open toward the first element is formed in the second element in the second contact face in such a way that the receiving space, during the relative movement of the first element with respect to the second element, can be brought into connection successively with the sample channel and with the dilution air channel.

The invention thus makes available a hand-held sampling head with a dilution principle which is of a kind different than the known valve technique and with which high dilution factors are also achievable without the need for an excessively large dilution air stream.

The invention affords the possibility of achieving these high dilution factors by a method in which, in contrast to the known valve techniques, the dilution air is not introduced into the sample volume but instead some of the sample volume is introduced into the dilution air.

Since the dilution principle realized in the sampling head according to the invention does not require valves, it is also unnecessary for the sample volume to be guided through a valve, which would lead to relatively rapid clogging of the valve in question.

For a space-saving arrangement of the dilution unit in the sampling head, provision can be made that the first element and/or the second element are/is disk-shaped. The contact faces can then be formed on a side face of the disk shape.

To realize the dilution principle, various relative movements between the elements are possible by which the at least one receiving space is guided to and fro between the sample channel and the dilution air channel.

From a mechanical aspect, relative movements without a reversal point are particularly expedient.

For example, provision can be made that the first element and the second element are arranged to be rotatable relative to each other about a rotation axis.

Thus, the at least one receiving space can be guided repeatedly to and fro between the sample channel and the dilution air channel.

Provision can be made that the first element is stationary. Thus, the delivery of the sample volume into the sample channel via the sample line and the delivery of the dilution air into the dilution air channel via the dilution air inlet can be carried out in a simple manner.

To realize the relative movement, provision can be made that the second element is mounted rotatably.

To make optimal use of the openings offered by the sample channel and by the dilution air channel, and to achieve thorough mixing between the at least one receiving space and the sample channel or dilution air channel, provision can be made that the sample channel and/or the dilution air channel are/is kidney-shaped along an arc of a circle. It is advantageous here that, during the relative movement, the at least one receiving space can be guided along the entire longitudinal extent of the sample channel or dilution air channel.

For the relative movement to be effected automatically, provision can be made that the second element is arranged in a rotationally fixed manner on a preferably motor-driven shaft.

Particularly good use of space and particularly good accessibility to the second element can be achieved if the shaft passes through the first element.

Provision can be made that the shaft is driven at that side of the first element directed away from the second element. It is advantageous that the second element can be easily fitted onto the shaft and removed therefrom for maintenance purposes without the drive connection of the driven shaft having to be canceled.

In order to achieve easy accessibility to the dilution unit for maintenance purposes and the like, provision can be made that the dilution unit is arranged under a cover cap, wherein the cover cap is connected to the rest of a housing of the sampling head.

For example, the cover cap can be connected detachably to the housing. A seal can be formed at the connection. It is particularly expedient if the cover cap is connected to the housing by a screw-type or bayonet-type closure.

To easily ensure that the first element comes into flat contact with the second element, provision can be made that a resilient element acts axially on the second element. The resilient element can be formed, for example, by a spring or by an elastically deformable solid body or the like.

In this case, provision can be made that the resilient element is supported on the cover cap. This has the advantage of permitting easy assembly of the dilution unit.

The flat contact of the first element with the second element at the respective contact faces can be made gas-tight, in order to prevent escape of gases/aerosols from the sample channel and dilution air channel or from the at least one receiving space.

To avoid wear at the contact faces, provision can be made that the first element and the second element are made from identical material. It is advantageous that both elements have identical degrees of hardness such that attrition is as low as possible.

It has been found that producing the first element and the second element from ceramic is particularly expedient and leads to a particularly stable dilution unit.

To avoid undesired, aggressive condensation in the dilution unit, provision can be made that a heating device is integrated for heating the dilution unit.

In this case, it is particularly expedient if the heating device is designed to heat the first element and/or the second element.

For example, this can be achieved by the heating device having a heating foil which lies flat on the first element or on the second element. It is advantageous that a heating foil takes up little space and that the flat contact permits good heat transfer to the heated element.

For example, provision can be made that the heating foil is arranged on that side of the first element directed away from the second element. Thus, being arranged away from movable parts, the heating foil can be protected from mechanical damage.

To better utilize the heating power of the heating device, provision can be made that the first element and/or the second element are/is enclosed by a heat-insulating capsule.

To avoid undesired, aggressive condensation and to avoid false measurement results, provision can be made that the sampling line has a heater. The heater preferably extends along the entire length or substantially the entire length of the sampling line.

In one embodiment of the invention, provision can be made that the dilution air channel, downstream of the dilution unit in the flow direction, is connected to a measuring tube made of electrically conductive material. For example, the measuring tube can be made from a chemically resistant, conductive tube, preferably of silicone enriched with carbon. It is advantageous that electrostatic charging of the measuring tube by particles suspended in the conveyed air can be avoided. Such electrostatic charging would lead to the removal of the suspended particles from the dilution air enriched for further measurements with suspended particles. This would lead to false measurement results.

A counting device can be configured for receiving spaces that are guided to and fro per unit of time between the sample channel and the dilution air channel. It is advantageous that the volume transported and exchanged per unit of time with the receiving space or the receiving spaces can be easily determined, for example by measuring a speed of rotation of a relative movement. The counting device can in this case be integrated into the sampling head or the analysis appliance of an analysis arrangement according to the invention.

If the speed of rotation of the driving motor is therefore regulated, it is then known, with very little error, how many receiving spaces per unit of time have transported a volume from the sample side to the dilution air side. The number times the volume of a receiving space yields the total transported volume of the sample. Since the suspended particles detected in a downstream particle determination unit can originate only from the sample stream, the dilution air stream can be variable within a range and does not have to be precisely regulated. The volumetric flows through the dilution unit do not therefore have to be strictly constant, which greatly reduces the demands on downstream pumps and on the flow resistances of the lines.

To achieve particularly precisely defined dilution ratios, provision can be made that the dilution air inlet is connected at one end or that end of the dilution air channel and the sampling line is connected at one end or that end of the sample channel in such a way that, with respect to the relative movement of the first element to the second element, flow directions in the same sense are defined. It is advantageous that the longest possible contact between the at least one receiving space and the respective channel can be achieved during the relative movement. Therefore, during the relative movement, the at least one receiving space comes into contact first with the end of the dilution air channel at which the dilution air inlet is located and first with the end of the sample channel at which the sampling line opens out.

Provision can also be made that the relative movement of the first element with respect to the second element is designed such that the at least one receiving space is guided along the dilution air channel counter to the flow direction through the latter. It is advantageous that good mixing between the volume contained in the receiving space and the volume contained in the dilution air channel can be achieved by eddies even at slow flow velocities.

In terms of the analysis arrangement described at the outset, the object of the invention is achieved by the fact that a sampling head according to the invention is connected to a portable analysis appliance.

It is advantageous that a measurement appliance is thus made available which is suitable for many areas of use, for example for monitoring the transport and production of substances/products with high particle contents, for general furnace plants and the like.

In order to limit the number of parts of the analysis arrangement that have to be individually handled, provision can be made that a dilution air filter is integrated in the analysis appliance and is connected to the dilution air inlet of the sampling head. It is additionally advantageous that a suction nozzle of the dilution air filter is arranged as far away as possible from the sampling head, such that there is largely no possibility of fractions of the sample reservoir getting into the dilution air in an uncontrolled manner.

To determine the masses of suspended particles in the aerosol, provision can be made that the analysis appliance has an impactor which is connected to the dilution air channel of the dilution unit. It is advantageous that the particularly high dilution factor attainable with the dilution unit according to the invention is well suited for the impactor measurement method.

In one embodiment of the invention, provision can be made that the analysis appliance has at least one sensor which is used to determine at least one gaseous constituent in the carrier gas of the aerosol and which is connected to the sample channel of the dilution unit. It is advantageous that the sample volume emerging practically or at least more or less undiluted from the dilution unit can be used for analysis of constituents. The resulting back-dilution can be easily corrected by computation.

Thus, in addition to determining the mass and/or number of the suspended particles (particle concentration and/or particle number in a particle size range) on the impactor, the analysis arrangement according to the invention is also able to measure the gas concentration (for example $O_2$ and CO or other constituents) in parallel, that is to say simultaneously or at a short time interval.

To comply with measurement ranges of the sensor, provision can be made that an additional dilution unit is arranged upstream of the sensor. The additional dilution unit is thus arranged downstream of the first dilution unit and preferably works according to another dilution principle, for example with the nozzle or valve technique. The dilution unit is preferably integrated in the analysis appliance.

For the operation of the impactor, provision can be made that the analysis appliance has a pump which is arranged downstream of the impactor in the suction direction. It is advantageous that the pump cannot corrupt the measurement result of the impactor.

Provision can also be made that the analysis appliance has a pump which is arranged upstream of the at least one sensor in the suction direction. It is advantageous that the sensor can be operated without pressure. The onward gas route downstream of the sensor can thus be designed to be open toward an exhaust.

Separate pumps are preferably formed for the impactor and the sensor, so as to be able to adapt optimally to the respective requirements.

In the method mentioned at the outset, the object is achieved, according to the invention, in that a sample stream, containing the aerosol, and a dilution air stream are delivered to a dilution unit, in that a predefined volumetric quantity of the sample stream and a predefined volumetric quantity of the dilution air stream are exchanged with each other in the dilution unit, in that the dilution air stream is delivered to a particle determination unit downstream of the dilution unit in the flow direction, which particle determination unit can determine a number and/or mass fractions of the suspended particles, and in that, downstream of the dilution unit in the flow direction, the sample stream is delivered to at least one sensor for determining at least one gaseous constituent in the carrier gas of the aerosol. The particle determination unit can be designed as a mass determination unit which is configured to calculate mass fractions of the suspended particles.

Thus, a determination of mass fractions of the suspended particles (for which a high dilution factor is needed) and a determination of constituents in the carrier gas (for which another dilution factor is needed) can both be realized simultaneously. As a result of the exchange according to the invention, two streams are obtained after the dilution, which streams can be used separately for different tasks, whereas, in the previously known valve technique, only one stream is made available after the dilution, which stream can be used either for the determination of mass fractions or for the determination of gaseous constituents.

The determination of the gaseous constituents can, for example, involve a determination of the nature of the constituents and/or a determination of the fractions of the constituents in the carrier gas.

For simple evaluation of the measurement results, provision can be made that a volumetric quantity in the dilution unit is exchanged per unit of time, by which a predefined dilution ratio in the dilution air stream is set.

If the exchange is achieved by a uniform relative movement, for example a uniform circular movement, between a first element containing a dilution air channel and a second element containing at least one receiving space, then the predefined dilution ratio can be easily set by means of the dilution air stream being generated with a constant volumetric flow.

To avoid undesired, aggressive condensation and contamination, provision can be made that the sample stream is heated upstream of the dilution unit, and/or that the dilution unit is heated.

To set a constant volumetric flow and/or to compensate for pressure fluctuations, provision can be made that the dilution air stream downstream of the particle determination unit is delivered through a buffer volume, followed by a capillary, to a pump.

To monitor the functionality of the particle determination unit and/or to regulate the pumping power, provision can be made that a pressure drop in the dilution air stream across the particle determination unit and/or the volumetric flow of the dilution air stream are/is measured. It is advantageous that a change of the dilution air stream, which can be caused by a clogged nozzle of an impactor in the particle determination unit for example, can be easily detected and indicated.

Provision can be made that the volumetric quantity is exchanged by at least one receiving space being brought into connection alternately with the sample stream and the dilution air stream. It is advantageous that the exchanged volumetric quantity can be easily predefined by the size of the at least one receiving space.

For example, provision can be made that the volumetric quantity exchanged per unit of time is measured. This is preferably done by counting how often per unit of time the at least one receiving space between the sample stream and the dilution air stream was moved to and fro. If the at least one receiving space is moved by a rotation movement between the dilution air stream and the sample stream, the counting can be carried out by means of the speed of the rotation movement being measured or predefined. By measuring the exchanged volumetric quantity, it is known how many suspended particles are contained in the dilution air, such that the measurement results of the particle determination unit can be easily evaluated and can be compared.

For example, provision can be made that the measured volumetric quantity is offset against at least one measurement result of the particle determination unit. It is advantageous that, in this way, a perhaps legally prescribed standardization of the measurement results of the particle determination unit can be achieved.

BRIEF DESCRIPTION OF THE DRAWINGS

The invention is now described on the basis of an illustrative embodiment, but it is not limited to this illustrative embodiment. Further illustrative embodiments result from combining individual features or several features of the claims with each other and/or with individual or several features of the illustrative embodiment.

DETAILED DESCRIPTION OF THE PREFERRED EMBODIMENTS

Figure 1:
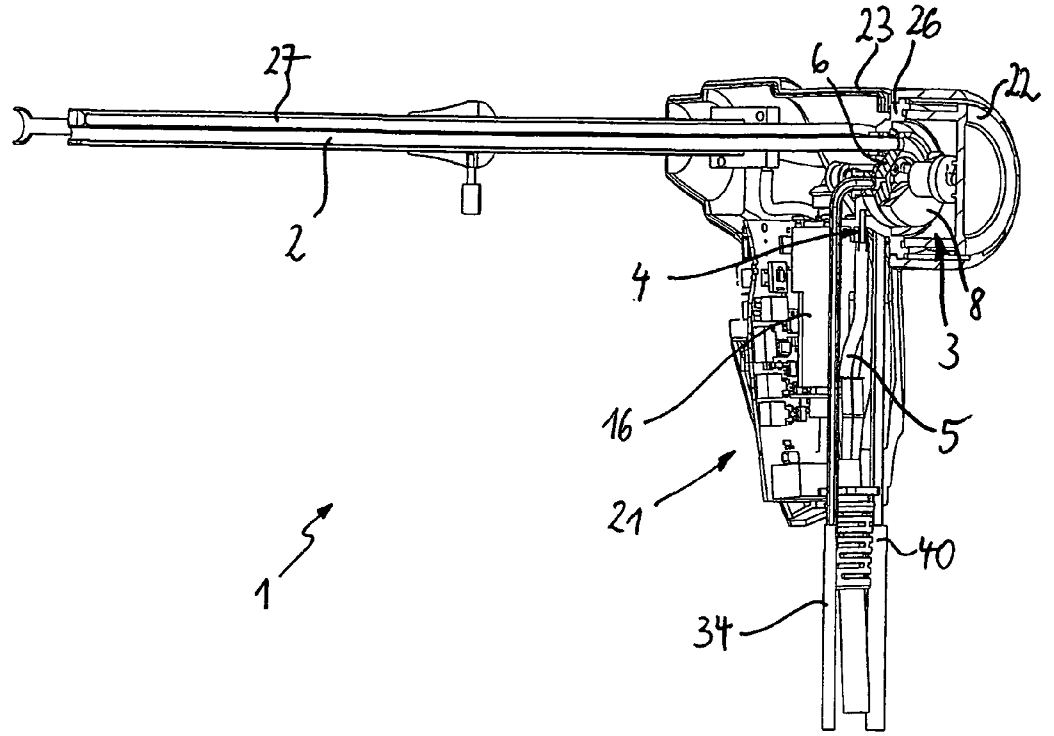
FIG. 1 shows a three-dimensional sectional view of a sampling head according to the invention.
Figure 2:
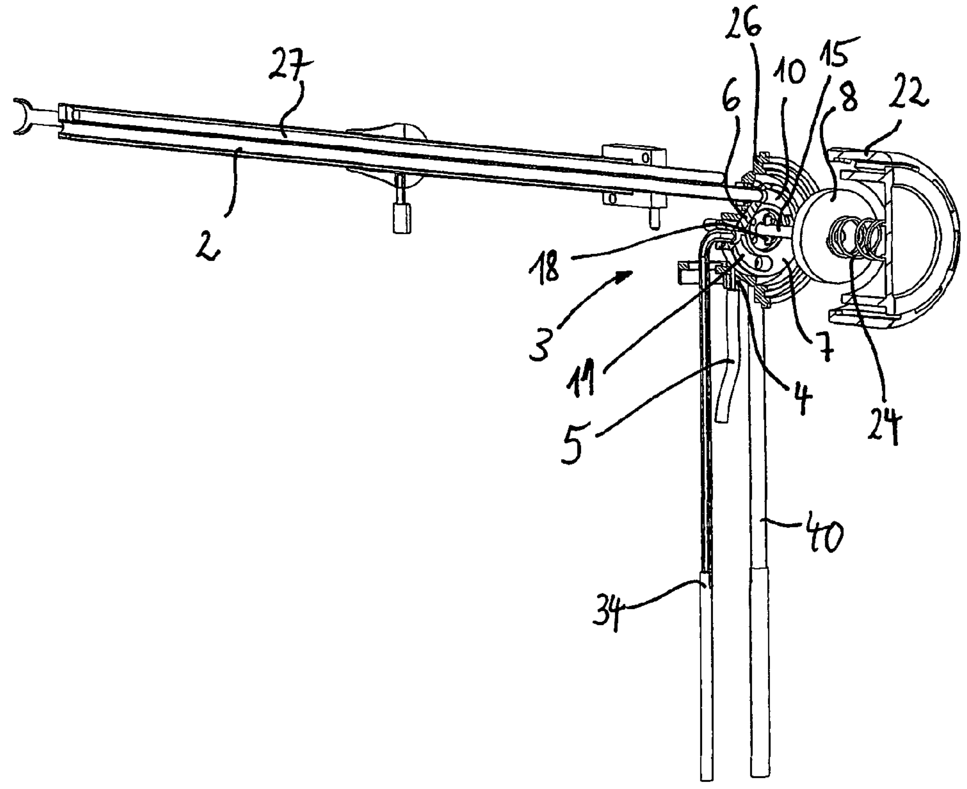
FIG. 2 shows the dilution unit of the sampling head from FIG. 1 in a partially exploded view.
Figure 3:
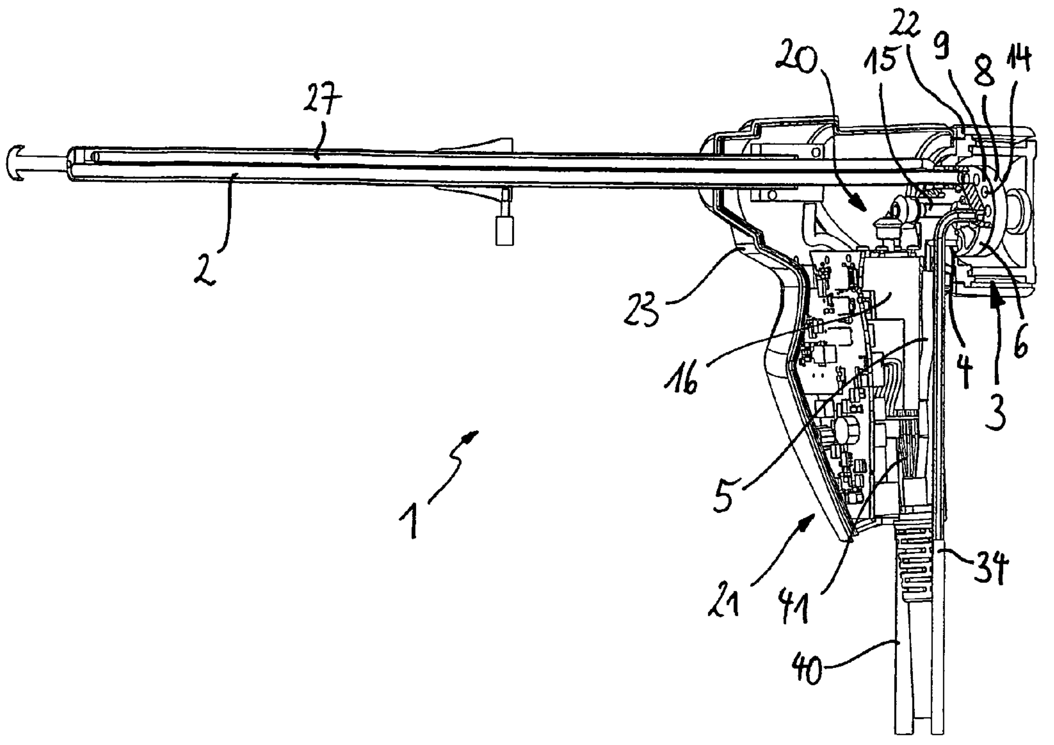
FIG. 3 shows the sampling head according to the invention from FIG. 1, in a three-dimensional sectional view seen from another angle.
Figure 4:
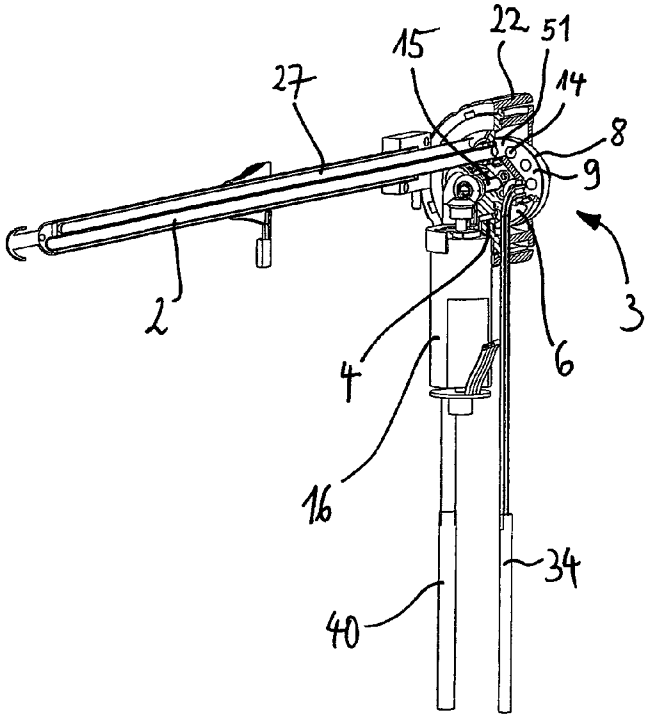
FIG. 4 shows the dilution unit of the sampling head from FIG. 1 in a three-dimensional sectional view seen from another angle.

FIGS. 1 to 9 show different views or component parts of a sampling head, designated overall by 1, and are therefore described jointly hereinbelow.

The sampling head 1 has a sampling line 2 via which an aerosol containing suspended particles is delivered to a dilution unit 3.

The dilution unit 3 also has a dilution air inlet 4, via which dilution air is delivered to the dilution unit 3 from a dilution air hose 5.

The dilution unit 3 has a first element 6, which is disk-shaped and provides a first contact face 7.

The dilution unit 3 also has a second element 8, which is likewise disk-shaped and of which the basic form corresponds to that of the first element 6.

The second element 8 provides a second contact face 9 which, in the position of use, lies flat and gas-tight on the first contact face 7.

Figure 6:
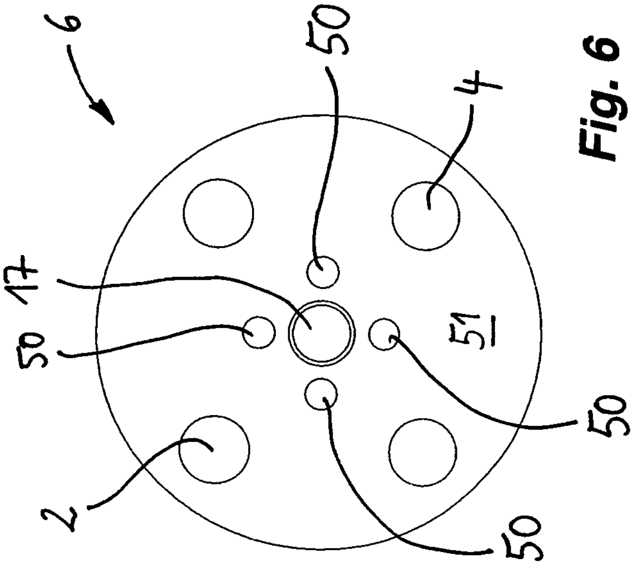
FIG. 6 shows the first element from FIG. 5 in a view from the opposite side.
Figure 5:
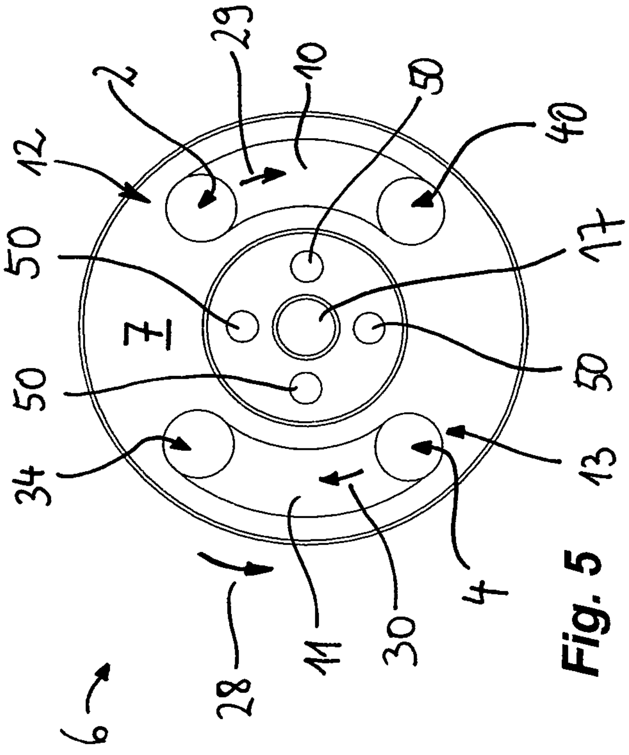
FIG. 5 shows a first element, according to the invention, of the dilution unit from FIG. 2, looking toward the contact face.
Figure 8:
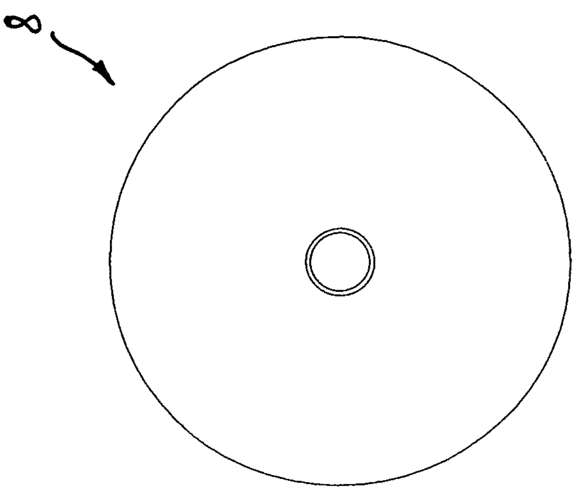
FIG. 8 shows the second element from FIG. 7 in a view toward the opposite side.
Figure 7:
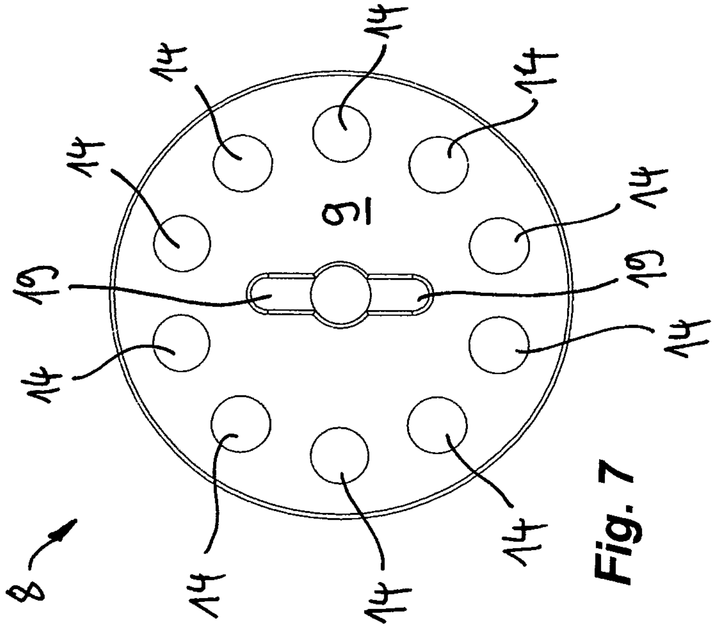
FIG. 7 shows the second element, according to the invention, of the dilution unit from FIG. 2, looking toward the contact face.
Figure 9:
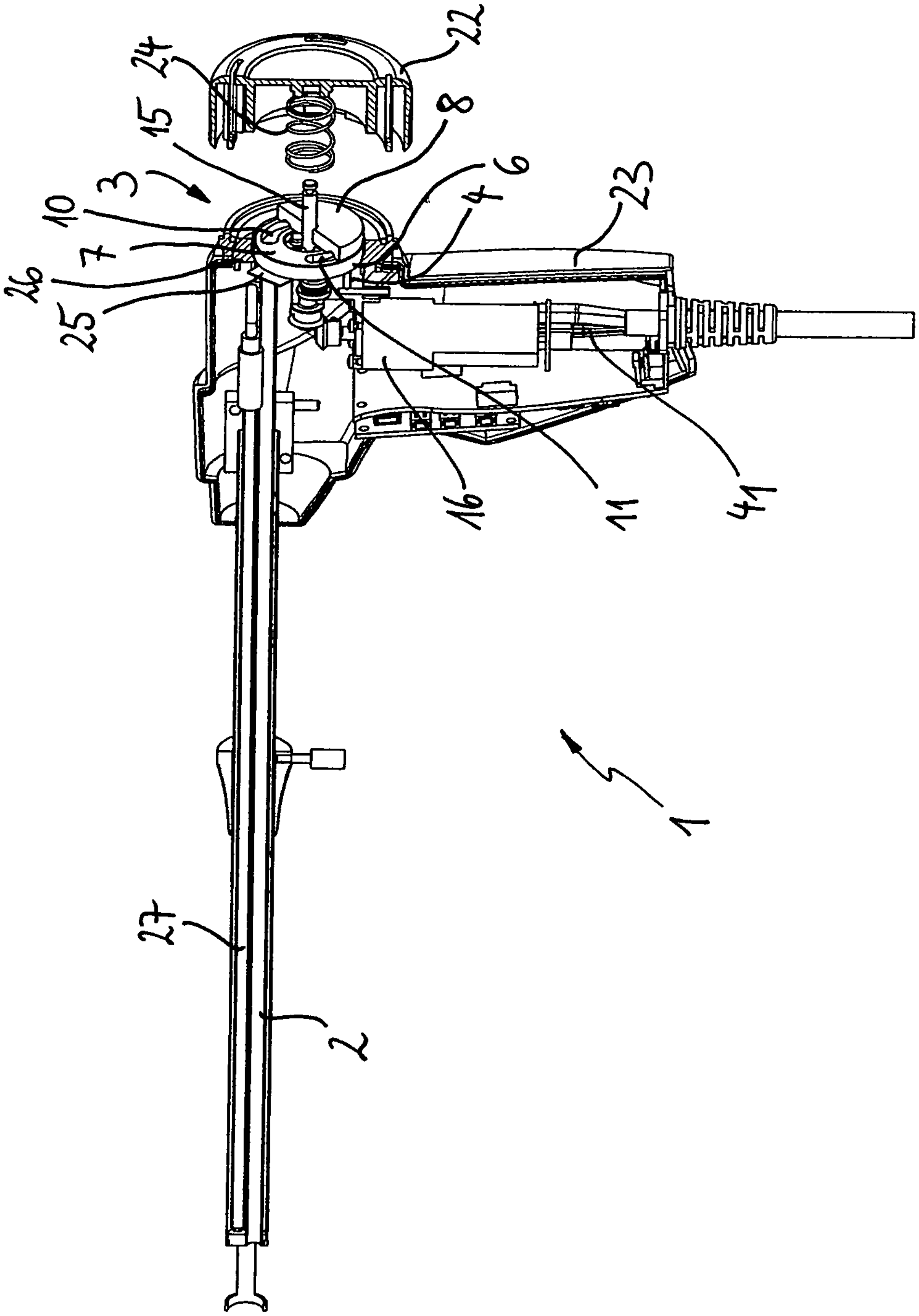
FIG. 9 shows a further three-dimensional sectional view of the sampling head from FIG. 1.

As can be seen in particular from the detailed views in FIG. 5 and FIG. 6, a sample channel 10 is formed in the first contact face 7 of the first element 6 and is open toward the second element 8 in the position of use.

In the first contact face 7, a dilution air channel 11 is also formed which is likewise open toward the second element 8 in the position of use.

The sample channel 10 and the dilution air channel 11 each extend in a kidney shape along an arc of a circle.

These arcs of a circle have a corresponding radius and a corresponding center, which coincides with the center of rotation of the second element 8.

The sample channel 10 is connected at one end 12 to the sampling line 2, while the dilution air channel 11 is connected at one end 13 to the dilution air inlet 4.

Ten receiving spaces 14 are formed as cavities in the second contact face 9 of the second element 8.

The receiving spaces 14 are arranged in a circle about the center point of the second element 8, which is at the same time the rotation point of the second element 8.

In further illustrative embodiments, other numbers of receiving spaces 14 are formed, for example a single receiving space, two or three receiving spaces 14, or more than three receiving spaces 14.

In the illustrative embodiment according to FIGS. 1 to 9, the receiving spaces 14 are arranged with respect to the center of rotation of the second element 8 in such a way that, upon rotation of the second element 8 with respect to the first element 6 in the position of use, the receiving spaces 14 are brought alternately into contact with the sample channel 10 and the dilution air channel 11 in succession.

A gas exchange or aerosol exchange is thus possible between the content of the receiving space 14 on the one hand and the sample channel 10 or dilution air channel 11 on the other hand, resulting in an exchange of a volumetric quantity, predefined by the size of the receiving spaces 14, between a sample stream flowing in the sample channel 10 and a dilution air stream flowing in the dilution air channel 11.

This has the effect that the dilution can be performed without a pressure increase on one side.

In the relative movement of the second element 8 with respect to the first element 6, which in the illustrative embodiment shown is a rotational movement or similar circular movement, the first element 6 remains stationary, while the second element 8 is connected to a shaft 15 for rotation therewith, which shaft 15 is driven by a motor 16.

For this purpose, the shaft 15 is guided through a central opening 17 of the first element 6 and engages right through this.

Drivers 18 extending in the radial direction are formed on the shaft 15 and engage in matching recesses 19 on the second element 8 for rotationally fixed connection of the second element 8 plugged onto the shaft 15.

The first element 6 is secured on the sampling head by securing means, which are inserted into four securing holes 50.

An operative connection between the driven shaft 15 and the electric motor 16 is produced via a conical stage 20, wherein the electric motor 16 can be arranged with its longitudinal axis in the direction of extent of the handle 21.

The dilution unit 3 is arranged under a detachable cover cap 22.

The cover cap 22 is hood-shaped and connected to the rest of the housing 23.

Between the second element 8 and the cover cap 22, a spring 24 (or another resilient element) is inserted which acts axially on the second element 8 and thus presses the first contact face 7 and the second contact face 9 onto each other for gas-tight closure.

The first element 6 and the second element 8 are made from ceramic material, for example by being cast, pressed, sintered and/or milled.

A heating foil 25 is placed flat on the rear face 51 of the first element 6 lying opposite the first contact face 7 and thus directed away from the second element 8, which heating foil 25, together with the associated electrical wiring (not shown), forms a heating device for heating the dilution unit 3.

The thereby heated first element 6 is enclosed in a shell-shaped capsule 26 which insulates the handle 21 and the housing 23 from the heat generated by the heating foil 25.

Along the sampling line 2, a heater 27 is formed with which the sampling line 2 can be kept above the condensation temperature of the aerosol.

The heating foil 25 is likewise operated at a temperature that prevents condensation in the dilution unit 3.

As can be seen more clearly from FIG. 5, the mouths of the sampling line 2 and of the dilution air inlet 4 are arranged at the ends 12, 13 of the sample channel 10 and of the air dilution channel 11 in such a way that, with respect to the relative movement 28, i.e. the rotation, of the second element 8 and the first element 6, mutually opposite flow directions 29, 30 are defined.

In the illustrative embodiment, the flow directions 29, 30 thus both have the opposite sense of rotation to the relative movement 28.

The indicated relative movement 28 designates the movement of the second element 8 in relation to the stationary first element 6.

Thus, the receiving spaces 14 are guided along the dilution air channel 11 in the flow direction 30 thereof.

Figure 10:
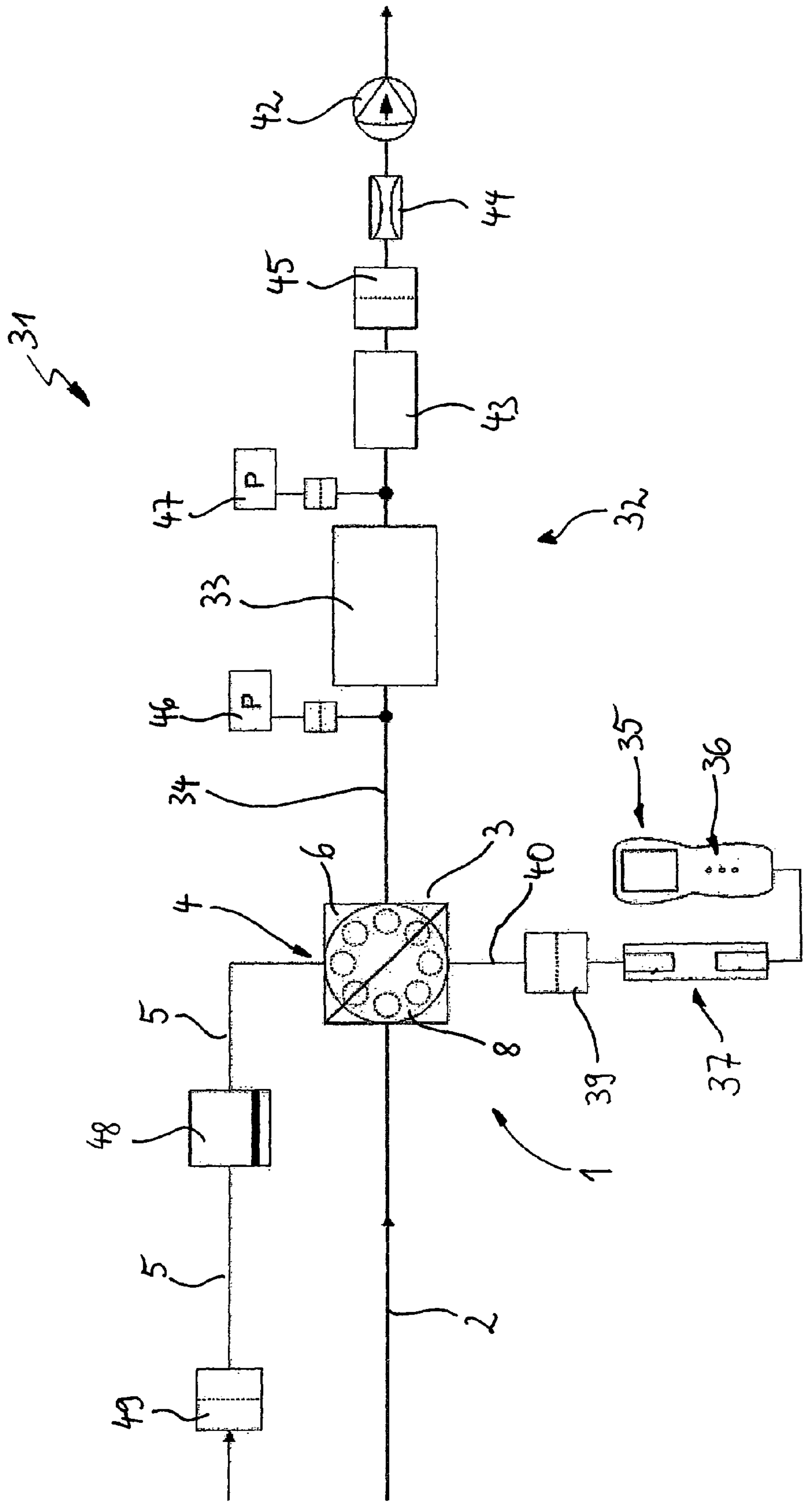
FIG. 10 shows the gas route plan of an analysis arrangement according to the invention.

The sampling head 1 shown in FIGS. 1 to 9 is used in an analysis arrangement 31, of which the gas route plan is shown in FIG. 10.

It will be seen that the sampling head 1 is connected to an analysis appliance, which is formed by the details shown in FIG. 10 in addition to the dilution unit 3 and the sampling line 2.

The analysis appliance of the analysis arrangement 31 accordingly has a particle determination unit 32 with an impactor 33, which is connected to the dilution air channel 11 via a measuring tube 34 (cf. FIGS. 1 to 5).

The measuring tube 34 is made from silicone enriched with carbon, which forms an electrically conductive material.

Mass fractions of the suspended particles in the aerosol can be determined with the particle determination unit 32.

The analysis appliance of the analysis arrangement 31 also has an integrated gas analyzer, which has one or more sensors for determining at least one gaseous constituent in the carrier gas of the aerosol.

Upstream of the gas analyzer 35 there are a combination appliance 37 (comprising a condensate trap and a fine filter) and a particle filter 39, which are connected to the outlet of the sample channel 10 by a sample line 40.

Dilution air hose 5, measuring tube 34 and sampling line 40, and also electrical leads 41, are routed to the analysis appliance inside a sheath (not shown).

The gas analyzer 35 is equipped with a pump (not shown) which generates a sample stream in the sample channel 10.

Downstream of the impactor 33, there is a further pump 42 with which a dilution air stream in the dilution air channel 11 can be generated.

To generate a uniform dilution air stream, a combination of a buffer volume 43 and of a capillary 44 downstream of the latter is provided for the pump 42. The capillary 44 is operated supercritically, such that an increase in the pump pressure does not cause any significant change of the delivery volume.

For protection of the capillary 44, a filter 45 is arranged between buffer volume 43 and capillary 44.

In a further illustrative embodiment, the capillary 44 and the filter 45 are not present.

In the sampling head 1, the speed of the motor 16 (cf. FIG. 1) is regulated. In the sampling head 1 or the analysis appliance (in particular the particle determination unit 32) of the analysis arrangement 31, a counting unit (not shown) is formed which, from the actual speed, derives the number of the receiving spaces 14 moved to and fro by the rotation between the sample channel 10 and the dilution air channel 11, wherein each receiving space 14 moved to and fro several times is counted several times. In this way, knowing the volume of a receiving space 14, it is possible to calculate the amount of the sample added to the dilution air. Thus, the measurement result on the particle determination unit can be normalized to this volumetric quantity and/or to a normal volume.

The impactor 33 of the illustrative embodiment according to FIG. 10 can be monitored by pressure sensors 46, 47, with which the pressure difference or pressure drop across the impactor 33 can be measured. The pumping power of the pump 42 is regulated on the basis of the measured pressure difference across the impactor 33.

The dilution air stream can be monitored by a dV/dT sensor 48, with which a volumetric flow of the dilution air stream can be measured.

With the buffer volume 43 and the capillary 44, a constant volumetric flow can be set for the dilution air stream, which is monitored by the pressure sensors 46, 47 and/or by the dV/dT sensor 48.

In the analysis appliance of the analysis arrangement 31, a filter 49 is also arranged for cleaning the dilution air sucked through the dilution air hose 5.

In the sampling head 1 of an analysis arrangement 31, provision is made that a sample stream delivered via a sampling line 2 and a dilution air stream delivered through a dilution air inlet 4 are mixed together in a dilution unit 3 in such a way that a volume quantity, entrained in at least one receiving space moved by a movable element 8, between the sampling stream and the dilution air stream is exchanged, wherein the analysis arrangement 31 has a gas analyzer 35 for the analysis of the slightly diluted sample stream and a particle determination unit 32 for the analysis of the enriched dilution air stream.

The invention claimed is:

1. A hand-held sampling head (1) for collecting a sample of an aerosol containing suspended particles, comprising a sampling line (2) and an integrated dilution unit (3) which is connected to the sampling line (2) and which has a dilution air inlet (4), the dilution unit (3) has a first element (6) with a first contact face (7) and a second element (8) with a second contact face (9), which are arranged to be movable relative to each other and which are in flat contact with each other via the respective contact faces (7, 9), a sample channel (10) open toward the second element (8) is formed in the first element (6) in the first contact face (7) and is connected to the sampling line (2), a dilution air channel (11) open toward the second element (8) is formed in the first element (6) in the first contact face (7) and is connected to the dilution air inlet (4) and to a tube for a particle determination unit, and at least one receiving space (14) open toward the first element (6) is formed in the second element (8) in the second contact face (9) in such a way that the receiving space (14), during a relative movement (28) of the first element (6) with respect to the second element (8), is brought into connection successively with the sample channel (10) and with the dilution air channel (11), and the first element (6) and the second element (8) are made from ceramic, and the dilution air inlet (4) is connected to the first element (6) at one end of the dilution air channel (11) on a side of the first element (6) which faces away from the second element (8) and the tube for the particle determination unit is also connected to the dilution air channel (11) on the side of the first element (6) which faces away from the second element (8).

2. The sampling head (1) as claimed in claim 1, wherein at least one of the first element (6) or the second element (8) are disk-shaped.

3. The sampling head (1) as claimed in claim 1, wherein the first element (6) is stationary, and the second element (8) is mounted rotatably.

4. The sampling head (1) as claimed in claim 1, wherein the second element (8) is arranged in a rotationally fixed manner on a driven shaft (15), or a shaft (15) passes through the first element (6), or the shaft (15) is driven at that side of the first element (6) directed away from the second element (8).

5. The sampling head (1) as claimed in claim 1, wherein the dilution unit (3) is arranged under a cover cap (22), the cover cap (22) is connected detachably to a housing (23) of the sampling head (1), or a resilient element acts axially on the second element (8), with the resilient element (24) being supported on a cover cap (22).

6. The sampling head (1) as claimed in claim 1, wherein the first element (6) and the second element (8) are made from identical material.

7. The sampling head (1) as claimed in claim 1, wherein a heating device (25) is integrated for heating the dilution unit (3), or a heating device has a heating foil (25) which lies flat on the first element (6) or on the second element (8), or a heating foil (25) is arranged on a side of the first element (6) directed away from the second element (8).

8. The sampling head (1) as claimed in claim 1, wherein at least one of the first element (6) or the second element (8) is enclosed by a heat-insulating capsule (26).

9. The sampling head (1) as claimed in claim 1, wherein the tube is connected to the dilution air channel (11) downstream of the dilution unit (3) in a flow direction (30), and the tube (34) is made of electrically conductive material.

10. The sampling head (1) as claimed in claim 1, wherein a plurality of receiving spaces are provided, and a counting device is configured for the receiving spaces (14) that are guided to and fro per unit of time between the sample channel (10) and the dilution air channel (11).

11. An analysis arrangement (31) for characterizing an aerosol, comprising a sampling head (1) as claimed in claim 1, connected to a portable analysis appliance.

12. The analysis arrangement (31) as claimed in claim 11, wherein a dilution air filter (49) is integrated in the analysis appliance and is connected to the dilution air inlet (4) of the sampling head (1), or the analysis appliance has an impactor (33) which is connected to the dilution air channel (11) of the dilution unit (3), or the analysis appliance has at least one sensor (36) which is used to determine at least one gaseous constituent in a carrier gas of the aerosol and which is connected to the sample channel (10) of the dilution unit (3).

13. The analysis arrangement (31) as claimed in claim 12, wherein the analysis appliance has a pump (42) which is arranged downstream of an impactor (33) in the suction direction, or the analysis appliance has a pump which is arranged upstream of the at least one sensor (36) in the suction direction.

14. The sampling head (1) as claimed in claim 1, wherein the first element (6) and the second element (8) are arranged to be rotatable relative to each other about a rotation axis.

15. The sampling head (1) as claimed in claim 1, wherein the first contact face (7) bears in a gas-tight manner on the second contact face (9).

16. The sampling head (1) as claimed in claim 1, wherein at least one of the sample channel (10) or the dilution channel (11) is kidney-shaped along an arc of a circle.

17. A method for characterizing an aerosol, said aerosol having a carrier gas and suspended particles received therein, the method comprising delivering a sample stream, containing the aerosol, and a dilution air stream to a dilution unit (3), exchanging a predefined volumetric quantity of the sample stream and a predefined volumetric quantity of the dilution air stream with each other in the dilution unit, delivering the dilution air stream to a particle determination unit (32) downstream of the dilution unit (3) in flow direction (30), using said particle determination unit (32) to determine at least one of a number or mass fractions of the suspended particles, and, downstream of the dilution unit (3) in flow direction (29), delivering the sample stream to at least one sensor (36) for determining at least one gaseous constituent in the carrier gas of the aerosol, and exchanging a volumetric quantity in the dilution unit (3) per unit of time, by which a predefined dilution ratio in the dilution air stream is set, and measuring the volumetric quantity exchanged per unit of time by counting how often per unit of time at least one receiving space (14) between the sample stream and the dilution air stream is moved to and fro.

18. The method as claimed in claim 17, wherein a volumetric quantity in the dilution unit (3) is exchanged per unit of time, by which a predefined dilution ratio in the dilution air stream is set, or the dilution air stream is generated with constant volume.

19. The method as claimed in claim 17, wherein at least one of the sample stream is heated upstream of the dilution unit (3), the dilution unit (3) is heated, the dilution air stream downstream of the particle determination unit (32) is delivered through a buffer volume (43), followed by a capillary (44), to a pump (42), or a pressure drop in the dilution air stream across the particle determination unit (32) or at least one of the volumetric flow of the dilution air stream is measured.

20. The method as claimed in claim 17, wherein at least one of the volumetric quantity is exchanged by at least one of the receiving spaces (14) being brought into connection alternately with the sample stream and the dilution air stream, or the volumetric quantity exchanged per unit of time is measured, by counting how often per unit of time the at least one receiving space (14) between the sample stream and the dilution air stream was moved to and fro.

* * * * *